United States Patent
Ware et al.

(10) Patent No.: US 6,704,597 B1
(45) Date of Patent: Mar. 9, 2004

(54) APPARATUS AND METHOD FOR ENERGY MANAGEMENT IN ATRIAL DEFIBRILLATOR

(75) Inventors: Kurt Ware, Vadnais Heights, MN (US); Jay A. Warren, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 263 days.

(21) Appl. No.: 09/620,686

(22) Filed: Jul. 20, 2000

(51) Int. Cl.[7] ................................................ A61N 1/38
(52) U.S. Cl. ............................................ 607/7; 607/14
(58) Field of Search ............................. 607/7, 4, 5, 14

(56) References Cited

U.S. PATENT DOCUMENTS

| | | | | |
|---|---|---|---|---|
| 4,830,006 A | * | 5/1989 | Haluska et al. ................ 607/4 |
| 5,111,813 A | * | 5/1992 | Charbonnier et al. .......... 607/8 |
| 5,179,945 A | * | 1/1993 | Van Hofwegen et al. ....... 607/5 |
| 5,207,219 A | * | 5/1993 | Adams et al. .................. 607/5 |
| 5,318,591 A | * | 6/1994 | Causey et al. ................. 607/5 |
| 5,395,373 A | | 3/1995 | Ayers ............................. 607/8 |
| 5,411,524 A | | 5/1995 | Rahul ............................. 607/4 |
| 5,480,413 A | | 1/1996 | Greenhut et al. ............. 607/14 |
| 5,554,174 A | | 9/1996 | Causey, III .................... 607/5 |
| 5,591,215 A | | 1/1997 | Greenhut et al. ............. 607/14 |
| 5,674,250 A | | 10/1997 | de Coriolis et al. ........... 607/7 |
| 5,840,079 A | | 11/1998 | Warman et al. ................ 607/4 |
| 5,999,850 A | | 12/1999 | Dawson et al. ................ 607/4 |

* cited by examiner

*Primary Examiner*—Angela D. Sykes
*Assistant Examiner*—Roderick Bradford
(74) *Attorney, Agent, or Firm*—Schwegman, Lundberg, Woessner & Kluth, P.A.

(57) ABSTRACT

An apparatus and method for delivering electrical shock therapy in order to treat atrial tachyarrhythmias such as fibrillation in which the energy stored in a capacitor used to deliver a shock pulse is monitored and adjusted. A charging circuit is used to charge the capacitor from a supply voltage upon detection of an atrial arrhythmia, and a controller monitors sensed ventricular depolarizations until R-wave synchrony requirements are met so that an atrial shock pulse can be safely delivered. The controller also attempts to maintain the voltage of the capacitor at a specified voltage before delivery of the shock pulse by operation of the charging circuit.

20 Claims, 2 Drawing Sheets

APPARATUS AND METHOD FOR ENERGY MANAGEMENT IN ATRIAL DEFIBRILLATOR

FIELD OF THE INVENTION

This invention pertains to systems and methods for treating atrial tachyarrhythmias. In particular, the invention relates to an apparatus and method for delivering shock therapy to terminate atrial fibrillation.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachycardia is characterized by a rapid rate but with an orderly contraction of the heart chamber, either due to an ectopic excitatory focus or abnormal excitation by normal pacemaker tissue. Fibrillation occurs when the chamber depolarizes in a chaotic fashion with abnormal depolarization waveforms as reflected by an EKG. An electrical shock applied to a heart chamber (i.e., defibrillation or cardioversion) can be used to terminate most tachyarrhythmias by depolarizing all excitable myocardium of the chamber, which thereby prolongs refractoriness, interrupts reentrant circuits, and discharges excitatory foci. Implantable cardioverter/defibrillators (ICDs) provide this kind of therapy by delivering a shock pulse to the heart when fibrillation is detected by the device. An ICD is a computerized device containing a pulse generator that is usually implanted into the chest or abdominal wall. Electrodes connected by leads to the ICD are placed on the heart, or passed transvenously into the heart, to sense cardiac activity and to conduct the impulses from the pulse generator. Typically, the leads have electrically conductive coils along their length that act as electrodes. ICDs can be designed to treat either atrial or ventricular tachyarrhythmias, or both, by delivering a shock pulse that impresses an electric field between the electrodes to which the pulse generator terminals are connected.

The most dangerous tachyarrhythmias are ventricular tachycardia and ventricular fibrillation, and implantable cardioverter/defibrillators (ICDS) have most commonly been applied in the treatment of those conditions. ICDs are also capable, however, of detecting atrial fibrillation and delivering a shock pulse to the atria in order to terminate the arrhythmia. Although not immediately life-threatening, it is important to treat atrial fibrillation for several reasons. First, atrial fibrillation is associated with a loss of atrioventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat AF offer a number of advantages to certain patients, including convenience and greater efficacy.

ICDs for delivering ventricular defibrillation shocks typically use a capacitor that is charged from a battery with an inductive boost converter to deliver the shock pulse. When ventricular fibrillation is detected, the ICD charges up the capacitor to a predetermined value for delivering a shock pulse of sufficient magnitude to convert the fibrillation (i.e., the defibrillation threshold). The capacitor is then connected to the shock electrodes disposed in the heart to deliver the shock pulse. Since ventricular fibrillation is immediately life threatening, these steps are performed in rapid sequence with the shock pulse delivered as soon as possible. Similarly, an ICD for treating atrial fibrillation charges an energy storage capacitor prior to delivering an atrial shock pulse once atrial fibrillation is detected. Additional constraints are presented in this situation, however. First, there is the risk that an atrial shock pulse can actually induce ventricular fibrillation, a condition much worse than atrial fibrillation. To lessen this risk, the ICD must ensure that the ventricular rhythm is regular and wait for an appropriate time window with respect to sensed ventricular depolarizations in which to deliver the atrial shock pulse. During this waiting period, the voltage of the energy storage capacitor begins to decay such that, in a typical electrolytic capacitor used in ICDs, the capacitor voltage can fall by 5% in 10 seconds. If the waiting period is long enough, the capacitor voltage may actually fall below the value necessary to deliver a shock pulse above the defibrillation threshold. It is this problem with which the present invention is primarily concerned.

SUMMARY OF THE INVENTION

The present invention is a method and apparatus for delivering atrial defibrillation therapy and managing the energy stored in a storage capacitor used to deliver the shock pulse. An exemplary embodiment of the invention includes sensing channels for sensing atrial and ventricular depolarizations, an energy storage capacitor switchably connected to shock electrodes for delivering a shock pulse to an atrium, and a charging circuit for charging the energy storage capacitor. A controller, which may include a programmable microprocessor, controls the operation of the device in accordance with sensed events. The controller starts the charging circuit upon detection of an atrial arrhythmia and charges the capacitor to a specified voltage corresponding to the programmed therapy energy. The controller then delivers an atrial shock pulse when ventricular depolarization synchrony requirements are met by switching the energy storage capacitor to the shock electrodes. Prior to delivery of the shock-pulse, the capacitor voltage is monitored, and the capacitor is recharged if the voltage has dropped below the specified voltage by a predetermined amount.

In a particular embodiment, the controller is configured to operate a boost converter to charge the capacitor to a specified capacitor voltage and to stop the boost converter when the capacitor voltage reaches the specified voltage. The controller is then further configured to restart the boost converter before a shock pulse is delivered if the capacitor voltage has dropped below the specified voltage by a predetermined amount. The voltage monitor may be implemented as a comparator for comparing a reference voltage with a voltage derived from a voltage divider connected to the energy storage capacitor. In a microprocessor-based implementation, the device may be programmed to check the voltage monitor after detection of an atrial arrhythmia when awakened by a sensed ventricular depolarization or by a timer expiration. The boost converter is then restarted if the voltage divider voltage has dropped below the reference voltage by a predetermined amount.

DESCRIPTION OF A SPECIFIC EMBODIMENT

Figure 1:
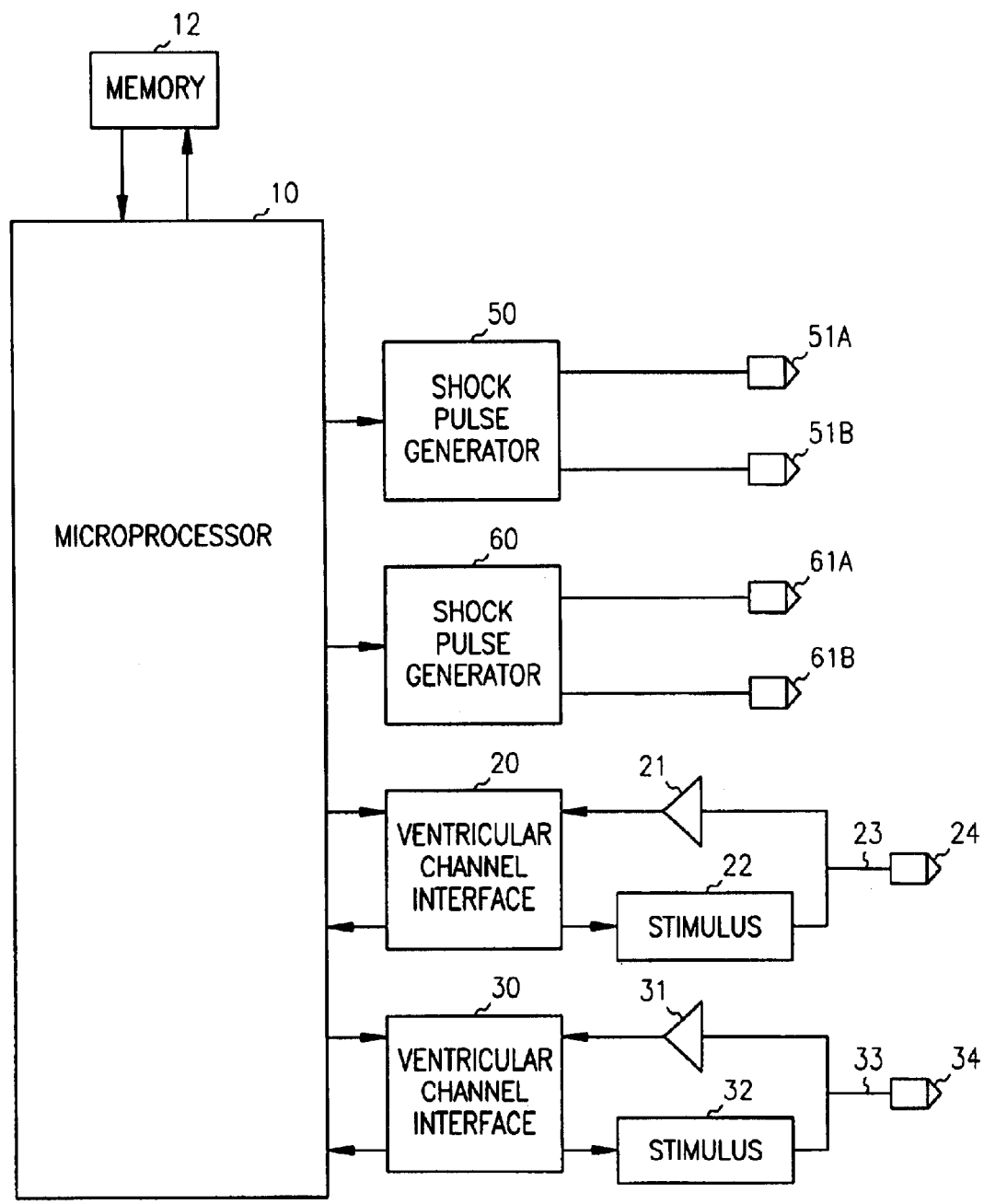
FIG. 1 is a system diagram of an implantable defibrillator.

FIG. 1 is a system diagram of a microprocessor-based implantable cardioverter/defibrillator device for treating atrial tachyarrhythmias that also incorporates a pacemaker functionality. In this embodiment, a microprocessor and associated circuitry make up the controller of the device, enabling it to output pacing or shock pulses in response to sensed events and lapsed time intervals. The microprocessor 10 communicates with a memory 12 via a bidirectional data bus. The memory 12 typically comprises a ROM or RAM for program storage and a RAM for data storage. The ICD has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The sensing channels are used to control pacing and for measuring heart rate in order to detect tachyarrhythmias such as fibrillation. The ICD detects an atrial tachyarrhythmia, for example, by measuring the atrial rate as well as possibly performing other processing on data received from the atrial sensing channel. A shock pulse generator 50 is interfaced to the microprocessor for delivering shock pulses to the atrium via a pair of terminals 51a and 51b that are connected by defibrillation leads to shock electrodes placed in proximity to regions of the heart. A similar shock pulse generator 60 and shock electrodes 61a and 61b are provided to deliver ventricular fibrillation therapy in the event of an induced ventricular fibrillation from atrial shock pulses. The defibrillation leads have along their length electrically conductive coils that act as electrodes for defibrillation stimuli. The defibrillation leads and electrodes may be implemented as lead-body electrodes that are either single elongated coils or made up of a plurality of smaller bands. The delivered voltage pulses may be either monophasic, biphasic, or multiphasic. The shock pulse generator as well as the rest of the circuitry are powered by a battery power supply. The device is enclosed by a housing which may be implanted by placing it an abdominal wall pocket, or preferably, in a pectoral pocket either subcutaneously or under the pectoralis major muscle. Typically, the leads from the housing are advanced to the heart transvenously, with venous access through the cephalic or subclavian veins. Each defibrillation lead is then connected to one of the pulse generator terminals.

Figure 2:
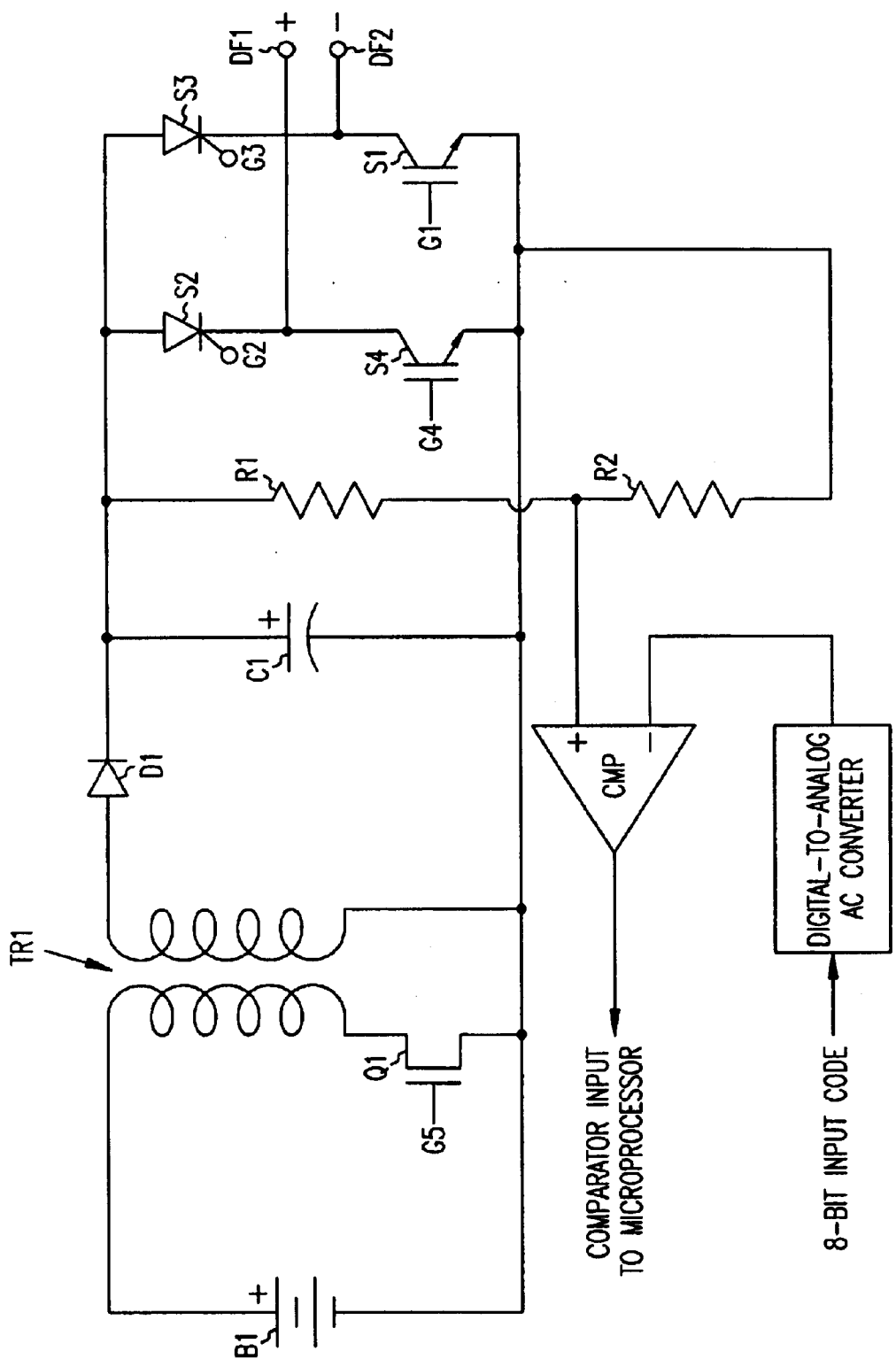
FIG. 2 is a diagram of the shock pulse generator.

FIG. 2 shows the components of the shock pulse generator 50 in more detail. The shock electrodes are connected to defibrillation terminals DF1 and DF2 which are switchably connected to an energy storage capacitor C1 by switches S1 through S4 in a so-called H-configuration. When a shock pulse is delivered, the defibrillation terminals are connected by the aforementioned switches to the capacitor C1 to thereby impress the capacitor voltage across the shock electrodes. Switches S1 and S2 are silicon controlled rectifiers having gate voltages G1 and G2, respectively, that are controlled by the microprocessor 10. Switches S3 and S4 are insulated gate bipolar transistors having microprocessor-controlled gate voltages G3 and G3. By controlling the state of the switches, the microprocessor can control the polarity of the shock pulse delivered to the electrodes as well as deliver monophasic or biphasic shock waveforms.

Before a shock pulse is delivered, the capacitor C1 is charged from battery B1 to a specified voltage by a charging circuit. The charging circuit in this embodiment is a boost converter which includes a transformer TR1 and a transistor switch Q1. Transistor Q1 is an FET having its gate voltage G5 connected to the output of an oscillator and includes circuitry for monitoring the drain current to avoid saturating the transformer core. The oscillator (not shown) is controlled by the microprocessor 10 and outputs pulses to switch current on and off in the primary coil of the transformer TR1. The width and/or frequency of the oscillator pulse output may also be controlled in accordance with the primary coil current sensed by transistor Q1. The coils of the transformer TR1 are coupled inductors that receive current from battery B1 during short intervals as dictated by the state of transistor Q1. When transistor Q1 is switched off, the energy stored in the inductance of the transformer is transferred to the capacitor C1 through a diode D1. The capacitor voltage is monitored by circuitry that includes a voltage divider, made up of resistors R1 and R2, and a comparator CMP. The voltage divider feeds the capacitor voltage to the comparator CMP where it is compared with a reference voltage specified by the microprocessor through digital-to-analog converter DAC. The comparator output is then input to the microprocessor which, as described below, controls the operation of the boost converter to maintain the capacitor voltage at an appropriate level.

The operation of the device is controlled by the microprocessor as follows. Data is received from the atrial and ventricular sensing channels reflecting depolarization activity, and if an atrial tachyarrhythmia is detected, the device prepares to deliver an atrial shock pulse by charging the capacitor C1 to a specified voltage. In order to avoid inducing a ventricular arrhythmia, the device then waits until ventricular depolarization synchrony requirements are met before delivering the atrial shock pulse. These requirements include a regular rhythm in which sensed ventricular depolarizations (i.e., R waves) are neither too far apart or too close together. If a regular ventricular rhythm is detected, the device waits for an appropriate time window with respect to a sensed R wave in which to deliver the atrial shock pulse. In an exemplary embodiment, the time window is between 10 and 70 ms after a sensed R wave. As noted above, during the time that the device waits to deliver the atrial shock pulse, the capacitor voltage decays from its initially charged value. In order to maintain the capacitor voltage at a value adequate for delivering a shock pulse, the microprocessor restarts the boost converter when the capacitor voltage has dropped below the specified voltage by a predetermined amount as indicated by the output of the comparator CMP. In particular embodiments, the microprocessor may be awakened during the waiting period to check the comparator output and restart the boost converter if necessary, either by a timer expiration or by sensed ventricular depolarizations. Once the boost converter is restarted, the capacitor C1 is charged until a specified value is reached as indicated by the voltage monitoring circuitry. When an appropriate time window for delivering the atrial shock pulse is detected, the microprocessor stops the boost converter if it is running and delivers the shock pulse by actuation of the switches S1 through S4.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An apparatus for delivering atrial defibrillation therapy, comprising:
   sensing channels for sensing atrial and ventricular depolarizations;
   a controller interfaced to the sensing channels, wherein the controller is configured to detect an atrial arrhythmia by measuring a rate of atrial depolarizations and to measure an interval between successive ventricular depolarizations in order to determine if ventricular depolarization synchrony requirements are met before delivering an atrial shock pulse;
   one or more shock electrodes;
   an energy storage capacitor switchably connected to the shock electrodes by the controller for delivering the atrial shock pulse;
   a charging circuit operated by the controller for charging the energy storage capacitor;
   a voltage monitor interfaced to the controller for monitoring the voltage of the energy storage capacitor;
   wherein the controller is configured to operate the charging circuit to charge the energy storage capacitor to a specified voltage upon detection of an atrial arrhythmia and to deliver the atrial shock pulse when ventricular depolarization synchrony requirements are met by switching the energy storage capacitor to the shock electrodes; and,
   wherein the controller is configured to monitor the capacitor voltage after detection of an atrial arrhythmia and to activate the charging circuit in order to recharge the capacitor prior to delivery of the atrial shock pulse if the capacitor voltage drops below the specified voltage by a predetermined amount.

2. The apparatus of claim 1 wherein the charging circuit is a boost converter which is started by the controller upon detection of the atrial arrhythmia.

3. The apparatus of claim 2 wherein the controller is configured to stop the boost converter when the capacitor voltage reaches the specified voltage.

4. The apparatus of claim 3 wherein the controller is configured to restart the boost converter before the atrial shock pulse is delivered if the capacitor voltage has dropped below the specified voltage by a predetermined amount.

5. The apparatus of claim 4 wherein the voltage monitor comprises a voltage divider connected to the energy storage capacitor and a comparator for comparing a reference voltage with a voltage derived from the voltage divider.

6. The apparatus of claim 2 wherein the controller includes a programmable microprocessor.

7. The apparatus of claim 6 wherein the microprocessor is programmed to be awakened by a sensed ventricular depolarization and to check the voltage monitor after detection of the atrial arrhythmia when awakened by the sensed ventricular depolarization and restart the boost converter if the capacitor voltage has dropped below the specified voltage by the predetermined amount.

8. The apparatus of claim 6 wherein the microprocessor is programmed to be awakened after a lapsed time interval and to check the voltage monitor after detection of an atrial arrhythmia when awakened and restart the boost converter if the capacitor voltage has dropped below the specified voltage by the predetermined amount.

9. The apparatus of claim 2 wherein the specified capacitor voltage is determined by a digital output from the controller.

10. The apparatus of claim 2 further comprising a supply voltage and wherein the charging circuit includes an inductor and a switch operated by the controller for switching current to the inductor from a supply voltage with the stored energy of the inductor then being transferred to the capacitor.

11. A method for delivering atrial defibrillation therapy, comprising:
    charging a capacitor to a specified voltage, the capacitor being switchably connected to electrodes for delivering a shock pulse to an atrium;
    monitoring ventricular depolarizations for a safe time window during which the shock pulse may be delivered and delivering the shock pulse if such a window is detected; and,
    monitoring the capacitor voltage after the capacitor has charged and prior to delivery of a shock pulse, and activating a charging circuit for recharging the capacitor if the capacitor voltage has dropped below the specified voltage by a predetermined amount.

12. The method of claim 11 further comprising charging the capacitor by starting a boost converter and stopping the boost converter when the capacitor has charged to the specified voltage.

13. The method of claim 12 further comprising restarting the boost converter before the atrial shock pulse is delivered if the capacitor voltage has dropped below the specified voltage by the predetermined amount and stopping the boost converter before delivering the shock pulse.

14. The method of claim 12 further comprising monitoring the capacitor voltage at periodic intervals after the boost converter is started.

15. The method of claim 12 further comprising monitoring the capacitor voltage upon detection of a ventricular depolarization after the boost converter is started.

16. The method of claim 12 further comprising restarting the boost converter if the capacitor voltage has dropped below the specified voltage by approximately 5 percent.

17. The method of claim 12 further comprising aborting the monitoring of the capacitor voltage if the shock pulse is not delivered within a specified time period after detection of an atrial arrhythmia.

18. The method of claim 12 further comprising monitoring the capacitor voltage at approximately 2 second intervals.

19. An apparatus for delivering atrial defibrillation therapy, comprising:

sensing channels for sensing atrial and ventricular depolarizations;

a controller interfaced to the sensing channels, wherein the controller is configured to detect an atrial arrhythmia by measuring a rate of atrial depolarizations and to measure an interval between successive ventricular depolarizations (R waves) in order to determine if ventricular depolarization synchrony requirements are met before delivering an atrial shock pulse;

one or more shock electrodes;

an energy storage capacitor switchably connected to the shock electrodes by the controller for delivering the atrial shock pulse;

means for charging the energy storage capacitor to a specified voltage upon detection of an atrial arrhythmia, monitoring the capacitor voltage after detection of the atrial arrhythmia, and activating the charging means for recharging the capacitor if the voltage drops below the specified voltage prior to delivery of the atrial shock pulse; and, wherein the controller is configured to deliver an atrial shock pulse when ventricular depolarization synchrony requirements are met by switching the energy storage capacitor to the shock electrodes.

20. The apparatus of claim 19 wherein the charging means comprises a boost converter operated by the controller and a voltage monitor for monitoring the voltage of the energy storage capacitor.

\* \* \* \* \*

UNITED STATES PATENT AND TRADEMARK OFFICE
CERTIFICATE OF CORRECTION

PATENT NO. : 6,704,597 B1
DATED : March 9, 2004
INVENTOR(S) : Ware et al.

It is certified that error appears in the above-identified patent and that said Letters Patent is hereby corrected as shown below:

Column 6,
Line 32, insert -- operating a --, before "charging".
Line 32, after "charging" insert -- circuit to charge --.
Line 32, after "voltage" insert -- upon detection of an atrial arrhythmia --.
Lines 39-43, delete "monitoring the capacitor voltage after the capacitor has charged and prior to delivery of a shock pulse, and activating a charging circuit for recharging the capacitor if the capacitor voltage has dropped below the specified voltage by a predetermined amount." and insert -- monitoring the capacitor voltage after detection of an atrial arrhythmia and activating the charging circuit in order to recharge the capacitor prior to delivery of the artial shock pulse if the capacitor voltage drops below the specified voltage by a predetermined amount. --, therefor.

Signed and Sealed this

Sixteenth Day of August, 2005

JON W. DUDAS
*Director of the United States Patent and Trademark Office*